(12) United States Patent
Corl

(10) Patent No.: US 12,193,876 B2
(45) Date of Patent: *Jan. 14, 2025

(54) INTRAVASCULAR DEVICES HAVING REINFORCED RAPID-EXCHANGE PORTS AND ASSOCIATED SYSTEMS AND METHODS

(71) Applicant: PHILIPS IMAGE GUIDED THERAPY CORPORATION, San Diego, CA (US)

(72) Inventor: Paul Douglas Corl, Palo Alto, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 324 days.

This patent is subject to a terminal disclaimer.

(21) Appl. No.: 17/669,562

(22) Filed: Feb. 11, 2022

(65) Prior Publication Data

US 2022/0160329 A1 May 26, 2022

Related U.S. Application Data

(63) Continuation of application No. 14/837,694, filed on Aug. 27, 2015, now Pat. No. 11,246,565.
(Continued)

(51) Int. Cl.
*A61B 8/00* (2006.01)
*A61B 5/00* (2006.01)
(Continued)

(52) U.S. Cl.
CPC ............ *A61B 8/445* (2013.01); *A61B 5/0066* (2013.01); *A61B 5/0084* (2013.01);
(Continued)

(58) Field of Classification Search
CPC ..... A61B 5/0066; A61B 8/445; A61B 8/4444; A61B 8/12; A61M 2025/0177; A61M 25/0052

See application file for complete search history.

(56) References Cited

U.S. PATENT DOCUMENTS

| | | |
|---|---|---|
| 5,243,988 A | 9/1993 | Wayne |
| 5,443,457 A | 8/1995 | Ginn |

(Continued)

FOREIGN PATENT DOCUMENTS

| | | |
|---|---|---|
| JP | H10500584 A | 1/1998 |
| JP | 2008079909 A | 4/2008 |

(Continued)

*Primary Examiner* — Angela M Hoffa

(57) ABSTRACT

Embodiments of the present disclosure are related to intravascular devices having improved rapid-exchange configurations and associated systems and methods. In some particular embodiments, the devices of the present disclosure include a reinforced rapid-exchange port, an offset rapid-exchange port, and/or combinations thereof. For example, in some implementations an intravascular imaging device is provided that includes a main catheter body; a rotational imaging element positioned within a lumen of the main catheter body; a distal portion extending from the main catheter body, the distal portion having a rapid-exchange port in communication with a guidewire lumen, the rapid-exchange port and the guidewire lumen sized and shaped to receive a guidewire; and at least one reinforcing element positioned adjacent to the rapid-exchange port.

12 Claims, 4 Drawing Sheets

Related U.S. Application Data

(60) Provisional application No. 62/042,978, filed on Aug. 28, 2014.

(51) Int. Cl.
  *A61B 8/08* (2006.01)
  *A61B 8/12* (2006.01)
  *A61B 8/14* (2006.01)
  *A61M 25/00* (2006.01)
  *A61M 25/01* (2006.01)

(52) U.S. Cl.
  CPC .......... *A61B 5/6851* (2013.01); *A61B 8/0891* (2013.01); *A61B 8/12* (2013.01); *A61B 8/14* (2013.01); *A61B 8/4444* (2013.01); *A61M 25/0052* (2013.01); *A61M 2025/0177* (2013.01)

(56) References Cited

U.S. PATENT DOCUMENTS

| | | |
|---|---|---|
| 5,546,948 A | 8/1996 | Hamm |
| 5,891,056 A | 4/1999 | Ramzipoor |
| 6,254,549 B1 | 7/2001 | Ramzipoor |
| 6,485,457 B1 | 11/2002 | Hisamatsu |
| 7,785,286 B2 | 8/2010 | Magnin |
| 7,815,627 B2 | 10/2010 | Von Oepen |
| 8,104,479 B2 | 1/2012 | Glynn |
| 8,491,567 B2 | 7/2013 | Magnin |
| 8,540,759 B2 | 9/2013 | Porter |
| 9,622,706 B2 | 4/2017 | Dick |
| 10,039,522 B2 | 8/2018 | Magnin |
| 10,156,448 B2 | 12/2018 | Geelen |
| 10,512,446 B2 | 12/2019 | Magnin |
| 11,246,565 B2 * | 2/2022 | Corl .................. A61B 8/445 |
| 2005/0070881 A1 | 3/2005 | Gribbons |
| 2006/0142703 A1* | 6/2006 | Carter ............... A61M 25/0043 264/138 |
| 2007/0016133 A1 | 1/2007 | Pepper |
| 2009/0018393 A1 | 1/2009 | Dick |
| 2009/0149936 A1 | 6/2009 | Lentz |
| 2010/0160788 A1 | 6/2010 | Davies |
| 2011/0137124 A1 | 6/2011 | Milner |
| 2012/0101561 A1 | 4/2012 | Porter |
| 2013/0303920 A1 | 11/2013 | Corl |
| 2014/0178574 A1 | 6/2014 | Van Hoven |
| 2014/0180076 A1 | 6/2014 | Stigall |
| 2014/0187959 A1 | 7/2014 | Corl |
| 2016/0029999 A1 | 2/2016 | Corl |

FOREIGN PATENT DOCUMENTS

| | | |
|---|---|---|
| JP | 2010500584 A | 1/2010 |
| JP | 20100533049 A | 10/2010 |
| JP | 2013544564 A | 12/2013 |
| WO | 1995923007 A1 | 8/1995 |
| WO | 2009085849 A2 | 7/2009 |

* cited by examiner

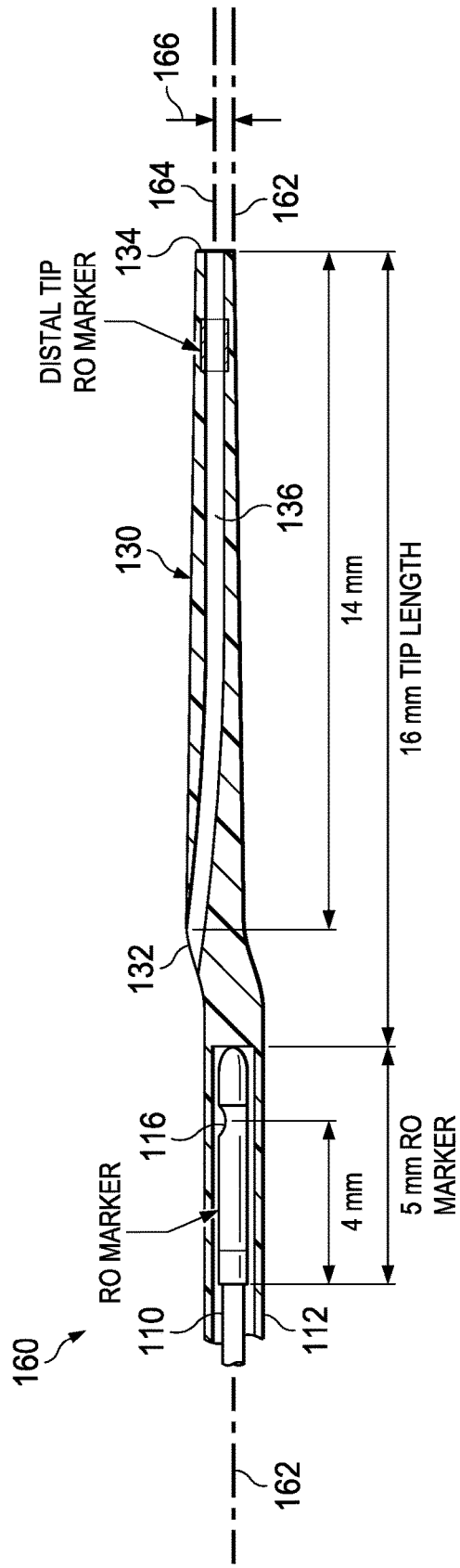
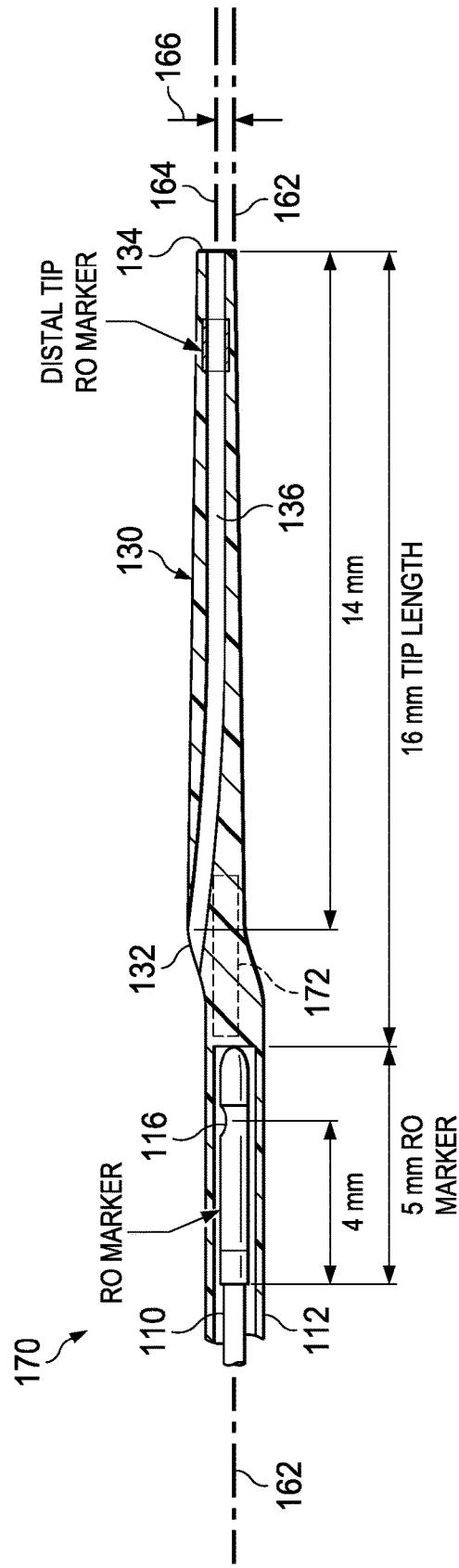

INTRAVASCULAR DEVICES HAVING REINFORCED RAPID-EXCHANGE PORTS AND ASSOCIATED SYSTEMS AND METHODS

CROSS REFERENCE TO RELATED APPLICATIONS

The present application is a continuation of U.S. application Ser. No. 14/837,694, filed Aug. 27, 2015, now U.S. Pat. No. 11,246,565, which claims priority to and the benefit of the U.S. Provisional Patent Application No. 62/042,978, filed Aug. 28, 2014, each of which is hereby incorporated by reference in its entirety.

TECHNICAL FIELD

The present disclosure relates generally to intravascular devices and, in particular, to catheters having a rapid-exchange port for receiving a guidewire.

BACKGROUND

In a traditional rapid-exchange interventional catheter (e.g., balloon catheter), with a long rapid exchange engagement (e.g., greater than 20 cm), the guidewire entry port on the catheter remains inside the guiding catheter throughout the interventional procedure. The guiding catheter constrains the guidewire to remain in close proximity and parallel to the interventional catheter, and it prevents either the guidewire or interventional catheter from bending significantly. Thus, when the guidewire is advanced, there is little possibility for the guidewire to buckle when resistance to movement within the rapid exchange lumen is encountered. Likewise, when the catheter is advanced over the guidewire, it is constrained from buckling/prolapse by the presence of the guiding catheter.

Rotational IVUS catheters and certain other interventional products (including OCT catheters) typically incorporate a relatively short rapid exchange segment at the tip of the catheter. The rotational IVUS catheter requires a very short rapid exchange tip to permit imaging in the distal segments of the coronary arteries. This short engagement length (typically ~25 mm) is not ideal and it increases the risk of catheter prolapse, and entanglement of the catheter and guidewire, potentially resulting in damage to one or both devices, or even trauma to the patient's artery as the prolapsed and or entangled devices are removed. However, this short engagement length is required for imaging in the distal portions of the coronary circulation, since the imaging core must terminate proximal to the location where the guidewire enters the catheter. If the guidewire were to engage the rapid exchange port back inside the guiding catheter, then the imaging core could not advance beyond the guiding catheter.

Although this short engagement length is essential for rotational IVUS catheters, there is a weakness in moving the rapid exchange entry port outside the guiding catheter and into the native artery, where there is significantly more lumen space and flexibility. If there is any resistance to guidewire movement through the rapid exchange lumen, then either of two problematic scenarios might arise: (1) advancing the guidewire can cause the guidewire to buckle or prolapse where it is hung up at the entry port, or (2) advancing the catheter might cause the catheter to buckle at the weak spot created by the rapid exchange entry port.

Accordingly, there remains a need for intravascular devices, systems, and methods that include an improved rapid-exchange port.

SUMMARY

Embodiments of the present disclosure are directed to intravascular devices having an improved rapid-exchange port.

In some implementations, an intravascular imaging device is provided that includes: a main catheter body; a rotational imaging element positioned within a lumen of the main catheter body; a distal portion extending from the main catheter body, the distal portion having a rapid-exchange port in communication with a guidewire lumen, the rapid-exchange port and the guidewire lumen sized and shaped to receive a guidewire; and at least one reinforcing element positioned adjacent to the rapid-exchange port. In some instances, the at least one reinforcing element extends from a position proximal of the rapid-exchange port to a position distal of the rapid-exchange port. The at least one reinforcing element can be a wire, a rod, a tapered rod, a tube, a u-shaped trough, and/or a spring coil and formed of a metal, a metal alloy, and/or a plastic. Further, in some instances the guidewire lumen extends offset, but parallel to a central axis of the main catheter body.

Associated systems and methods are also provided. For example, in some implementations a processing system is in communication with the intravascular imaging device. The processing system can be configured to process data obtained by the intravascular imaging device. Further, the system can include a patient interface module configured to interface with a proximal portion of the intravascular imaging device and communicate with the processing system. A display in communication with the processing system can be utilized to visualize information obtained by the intravascular imaging device.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 7 is a cross-sectional side view of a distal portion of an intravascular device having a rapid-exchange port according to an embodiment of the present disclosure.

FIG. 8 is a cross-sectional side view of a distal portion of an intravascular device having a reinforced rapid-exchange port according to an embodiment of the present disclosure.

DETAILED DESCRIPTION

Figure 1:
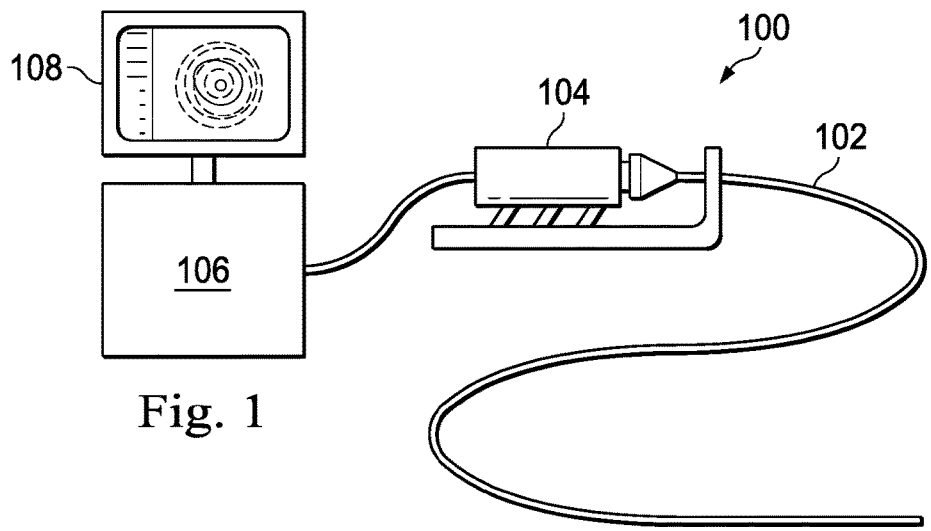
FIG. 1 is a diagrammatic schematic view of an intravascular imaging system according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Referring to FIG. 1, shown therein is an IVUS imaging system 100 according to an embodiment of the present disclosure. In some embodiments of the present disclosure, the IVUS imaging system 100 is a rotational IVUS imaging system. In that regard, the main components of the rotational IVUS imaging system are the rotational IVUS catheter 102, a patient interface module (PIM) 104, an IVUS console or processing system 106, and a monitor 108 to display the IVUS images generated by the IVUS console 106.

Figure 2:
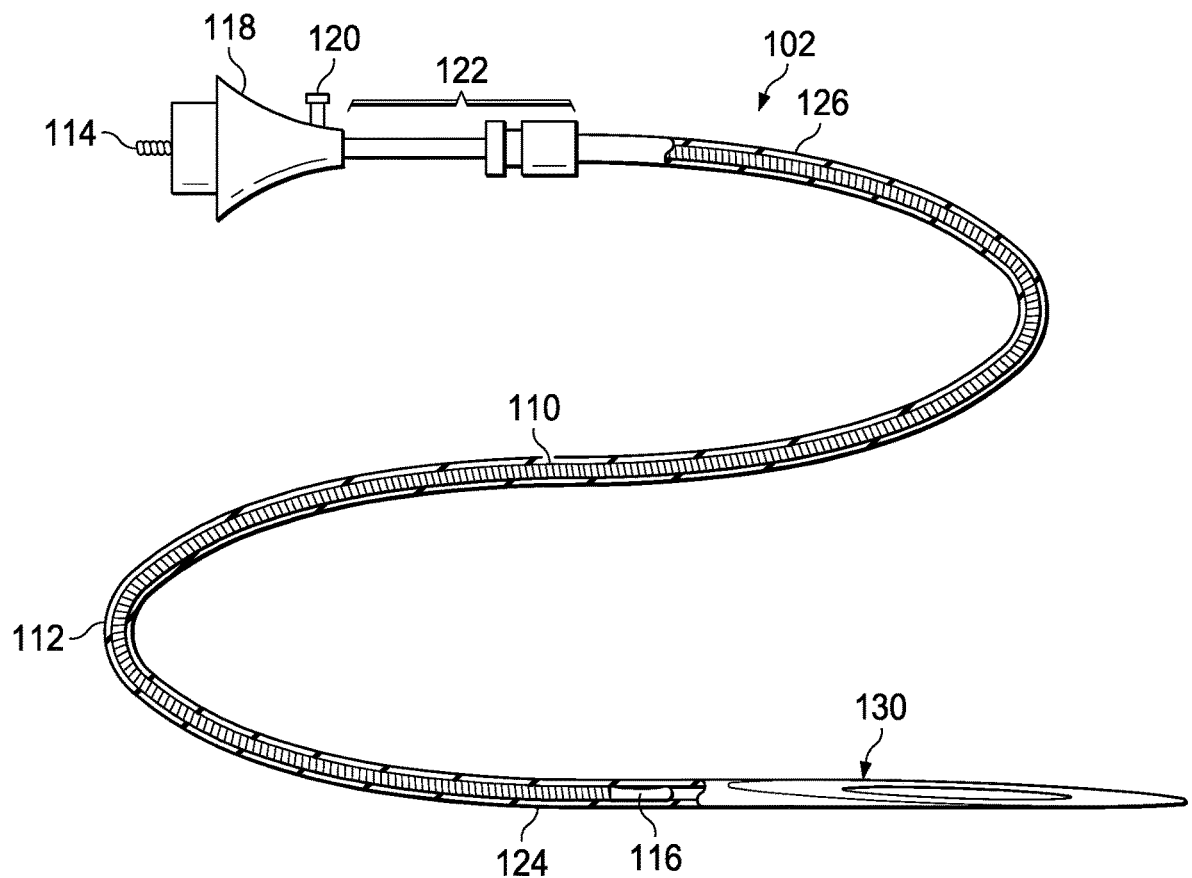
FIG. 2 is a partial cutaway, perspective view of an intravascular device according to an embodiment of the present disclosure.

Referring now to FIG. 2, shown therein is a diagrammatic, partial cutaway perspective view of the rotational IVUS catheter 102 according to an embodiment of the present disclosure. In that regard, FIG. 2 shows additional detail regarding the construction of the rotational IVUS catheter 102. In many respects, this catheter is similar to traditional rotational IVUS catheters, such as the Revolution® catheter available from Volcano Corporation and described in U.S. Pat. No. 8,104,479, or those disclosed in U.S. Pat. Nos. 5,243,988 and 5,546,948, each of which is hereby incorporated by reference in its entirety. In that regard, the rotational IVUS catheter 102 includes an imaging core 110 and an outer catheter/sheath assembly 112. The imaging core 110 includes a flexible drive shaft that is terminated at the proximal end by a rotational interface 114 providing electrical and mechanical coupling to the PIM 104 of FIG. 1. The distal end of the flexible drive shaft of the imaging core 110 is coupled to a housing 116 containing the ultrasound transducer and, in some instances, associated circuitry. It is understood that in other embodiments, the IVUS catheter is an optical coherence tomography (OCT) catheter and, in such embodiments the housing 116 can contain corresponding portions of the OCT catheter, such as optical fiber(s) and optical imaging element(s) (e.g., mirrors, prisms, scanners, etc.).

The catheter/sheath assembly 112 includes a hub 118 that supports the rotational interface and provides a bearing surface and a fluid seal between the rotating and non-rotating elements of the catheter assembly. The hub 118 includes a luer lock flush port 120 through which saline is injected to flush out the air and fill the inner lumen of the sheath with an ultrasound-compatible fluid at the time of use of the catheter. The saline or other similar flush is typically required since air does not readily conduct ultrasound. Saline also provides a biocompatible lubricant for the rotating driveshaft. The hub 118 is coupled to a telescope 122 that includes nested tubular elements and a sliding fluid seal that permit the catheter/sheath assembly 112 to be lengthened or shortened to facilitate axial movement of the transducer housing within an acoustically transparent window 124 of the distal portion of the catheter 102. In some embodiments, the window 124 is composed of thin-walled plastic tubing fabricated from material(s) that readily conduct ultrasound waves between the transducer and the vessel tissue with minimal attenuation, reflection, or refraction. A proximal shaft 126 of the catheter/sheath assembly 112 bridges the segment between the telescope 122 and the window 124, and is composed of a material or composite that provides a lubricious internal lumen and optimum stiffness, but without the need to conduct ultrasound.

Figure 3:
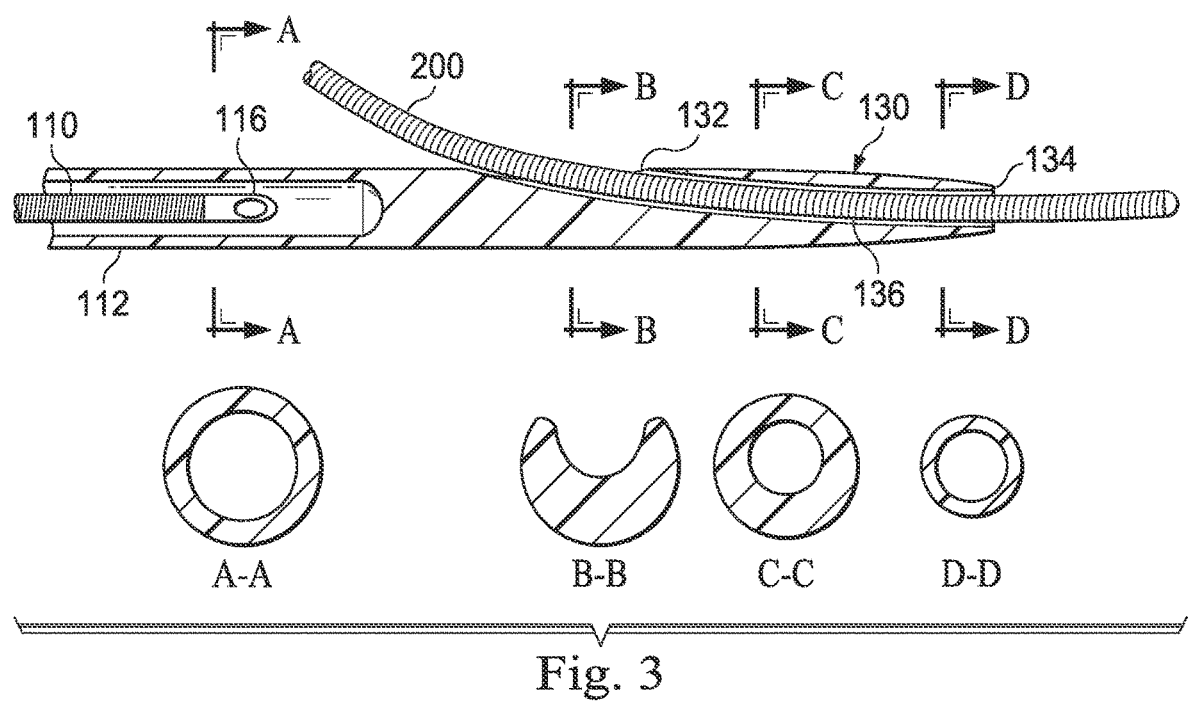
FIG. 3 is a cross-sectional side view of a distal portion of an intravascular device receiving a guidewire through a rapid-exchange port according to an embodiment of the present disclosure along with a plurality of cross-sectional end views at section lines A-A, B-B, C-C, and D-D along the length of the distal portion of the intravascular device.

The rotational IVUS catheter 102 also includes a distal portion 130 configured to receive a guidewire. In particular, as shown in FIG. 3, the distal portion 130 includes a rapid-exchange configuration that includes an opening or port 132 in a sidewall of the catheter 102, an opening or port 134 at the distal tip of the catheter 102, and a lumen 136 extending between the ports 132 and 134 such that a guidewire 200 can extend through the port 132, along the lumen 136, and out of the port 134, as shown. In that regard, the guidewire 200 can be utilized to guide advancement of the catheter 102 to a desired location within a patient. In the illustrated embodiment of FIG. 3, the lumen 136 extends substantially coaxial with the drive shaft 110 and/or central axis of the proximal portion of the catheter 102. However, as described in the context of FIGS. 7 and 8 below, in some instances the lumen 136 of the distal portion 130 is offset relative to the drive shaft 110 and/or central axis of the proximal portion of the catheter 102.

Figure 4:
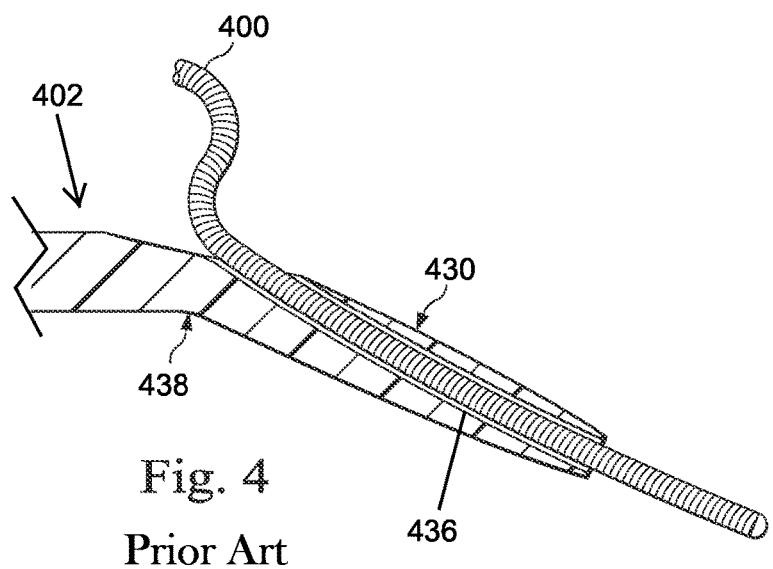
FIG. 4 is a cross-sectional side view of a distal portion of an intravascular device receiving a guidewire through a rapid-exchange port in a prolapsed position.

FIG. 3 also illustrates the cross-sectional profiles of the catheter body at various positions along the length of the catheter 102. As shown, at section lines A-A, C-C, and D-D the catheter body has a complete circular cross-sectional profile, whereas at section line B-B, where the rapid-exchange port 132 is located, the catheter body has a generally u-shaped cross-sectional profile. As a result, the catheter 102 can be prone to bending at section line B-B, particularly in the plane of the guidewire. For example, FIG. 4 shows a cross-sectional side view of the distal portion 430 of the catheter 402 in such a prolapsed position. This is a failure mode of concern, where advancing the guidewire 400 or retracting the catheter might cause the guidewire 400 to buckle, and/or the catheter 402 to bend at an exchange joint 438. Ideally, the guidewire 400 would simply slide through the rapid-exchange lumen 436 and the guidewire 400 and catheter 402 would remain substantially coaxial and/or parallel to one another. However, once this failure mode begins to occur, it is likely to persist, as the catheter 402 may plastically deform at the exchange joint 438 and assume a persistent bend, possibly compressing the lumen 436 to cause further resistance to guidewire movement relative to the catheter. In addition, the guidewire 400 may be deformed where it prolapses, predisposing the guidewire 400 to collapse at the same location as the guidewire 400 is advanced or as the catheter 402 is retracted.

Embodiments of the present disclosure address these issues by reinforcing the catheter body at the location of the rapid-exchange port 132 to avoid the sudden transition in bending stiffness that can occur at that location due to the change in cross-sectional profile of the catheter body, which can make the device vulnerable to prolapse. In that regard, typically the notch or opening formed by the rapid-exchange port 132 on the side of the catheter 102 creates a weak spot and a sharp discontinuity in bending stiffness that makes the catheter prone to prolapse at that location. Catheter prolapse can also cause the guidewire lumen 136 to collapse in such a way that it grabs or pinches the guidewire 200, further exacerbating the problem. As a result, embodiments of the present disclosure improve the rapid-exchange functionality of the catheter 102 by reducing guidewire binding and catheter prolapse while simultaneously improving patient safety.

One or more stiffening elements can be utilized to reinforce the weak segment in the catheter 102 created by the presence of the notch or opening in the side of the catheter body defining the rapid-exchange entry port 132. The stiffening element(s) can be a metal or plastic structure positioned inside the body of the catheter to bridge the weak segment at the exchange joint 138. In that regard, the stiffening element(s) can take on many variations in materials, sizes, shapes, orientations, to achieve the desired reinforcement across the rapid-exchange joint 138. For example, suitable materials include metals and metal alloys (stainless steel, Nitinol, etc.) as well as any relatively stiff plastics (PEEK, Nylon, high durometer Pebax, polyimide, etc.). Further, the stiffening element(s) can have any number of structural shapes (wire, rod, tapered rod, tube, u-shaped trough, spring coil, etc.) and can be arranged within the catheter body in both symmetrical and non-symmetrical orientations. In some implementations, the stiffening element(s) can be a custom-molded part designed to maintain the optimum mechanical properties in the vicinity of the rapid-exchange port 132, while incorporating features to facilitate bonding to both the proximal catheter tubing and the distal catheter tip. Generally, the reinforced exchange joint 138 should maintain a bending stiffness to match (or smoothly transition from) the properties of the catheter 102 just proximal of the rapid-exchange entry port 132 to those just distal of the port 132. Accordingly, the stiffening element(s) should not be excessively rigid to avoid introducing bending stiffness discontinuities in other locations along the catheter 102 and/or make it difficult to navigate the catheter around tight curves in the coronary arteries.

Figure 5:
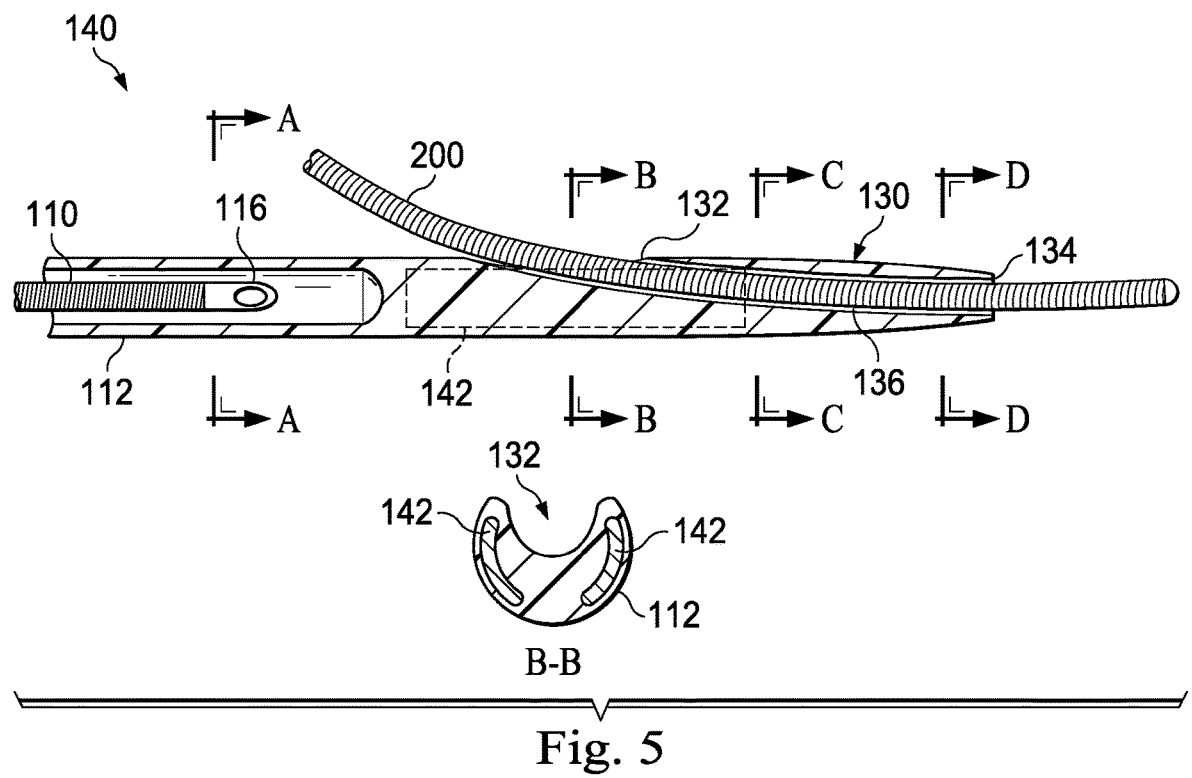
FIG. 5 is a cross-sectional side view of a distal portion of an intravascular device receiving a guidewire through a reinforced rapid-exchange port according to an embodiment of the present disclosure along with a cross-sectional end view of the reinforced rapid-exchange port along section line B-B.
Figure 6:
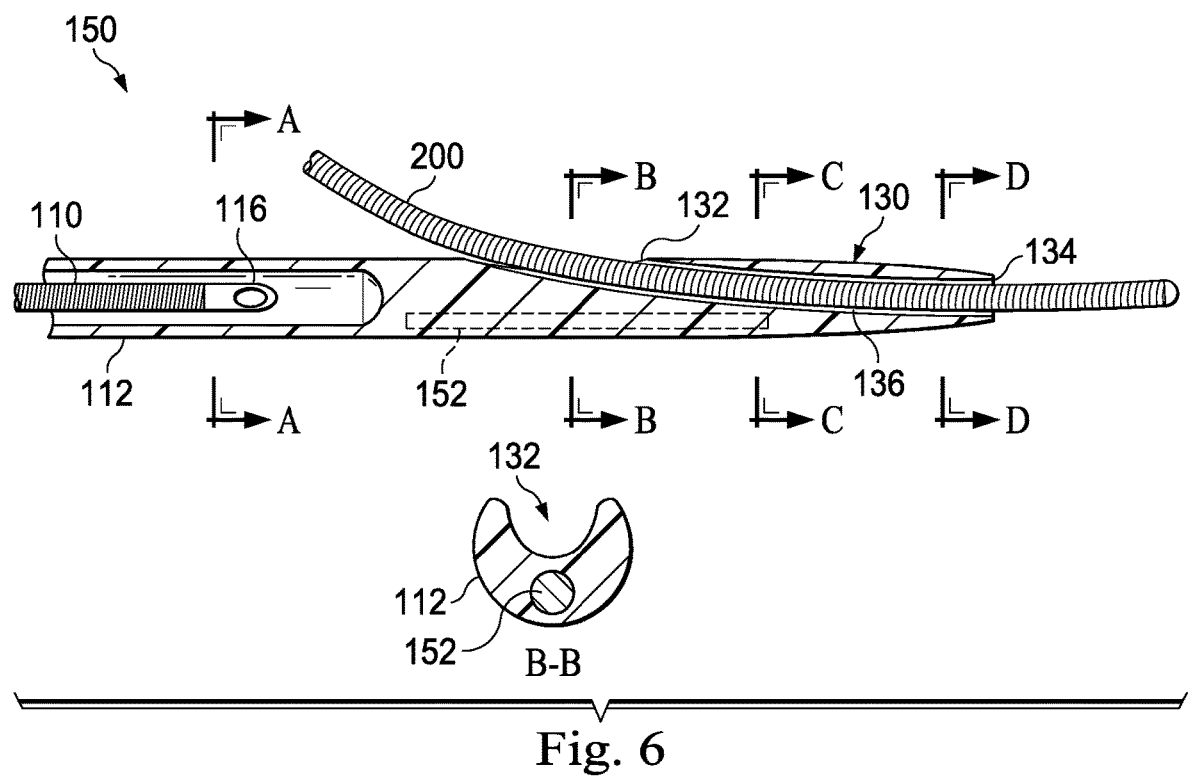
FIG. 6 is a cross-sectional side view of a distal portion of an intravascular device receiving a guidewire through a reinforced rapid-exchange port according to another embodiment of the present disclosure along with a cross-sectional end view of the reinforced rapid-exchange port along section line B-B.

Referring now to FIGS. 5 and 6, shown therein are exemplary embodiments of catheters including a reinforced rapid-exchange configuration in accordance with the present disclosure. For example, FIG. 5 illustrates an embodiment of a distal portion 140 of an imaging catheter having a pair of reinforcing elements 142 positioned within the catheter body adjacent to the rapid-exchange entry port 132. In particular, as shown the reinforcing elements 142 extend longitudinally along the length of the catheter body from a position just proximal of the rapid-exchange entry port 132 to a position distal of the rapid-exchange entry port 132. Further, as shown in the cross-sectional view along section line B-B the reinforcing elements 142 are positioned opposite one another on opposing sides of the catheter body next to the rapid-exchange entry port 132. In this manner, the reinforcing elements 142 provide reinforcement and support to the catheter body across the rapid-exchange entry port 132 as discussed above.

FIG. 6 illustrates another embodiment of a distal portion 150 of an imaging catheter having a stiffening element 152 positioned within the catheter body adjacent to the rapid-exchange entry port 132. In particular, as shown the stiffening element 152 extends longitudinally along the length of the catheter body from a position just proximal of the rapid-exchange entry port 132 to a position distal of the rapid-exchange entry port 132. Further, as shown in the cross-sectional view along section line B-B the reinforcing element 152 is positioned within the catheter body directly below the rapid-exchange entry port 132. In this manner, the reinforcing element 152 provide reinforcement and support to the catheter body across the rapid-exchange entry port 132 as discussed above.

Referring now to FIGS. 7 and 8, shown therein are exemplary embodiments of catheters including an offset rapid-exchange configuration in accordance with the present disclosure. In that regard, each of FIGS. 7 and 8 illustrate an optical coherence tomography (OCT) catheter where the distal portion 130 is offset with respect to the proximal portion of the catheter. For example, FIG. 7 shows an OCT catheter 160 where the distal portion 130 is offset such that the lumen 136 of the distal portion 130 is offset relative to the drive shaft 110 and/or central axis 162 of the proximal portion of the catheter 160. As shown, a central axis 164 of the distal portion 130 and/or the lumen 136 is offset with respect to the central axis 162 of the proximal portion of the catheter 160 by a distance 166. In some instances, the distance 166 is between about 0.25 mm (0.010") and about 0.75 mm (0.030"). In that regard, in some embodiments the distal portion 130 has an outer diameter of approximately 0.5 mm and an inner lumen diameter of approximately 0.35 mm, while the main body of the catheter 160 has an outer diameter of approximately 1.0 mm. However, it is understood that the concepts of the present disclosure are equally applicable to catheters having other sizes. The offset between the distal portion 130 and the main body of the catheter 160 allows the guidewire 200 to remain closer to parallel with the catheter shaft (i.e., with less bending) where it emerges from the rapid-exchange entry port 132 compared to a traditional design where the central axis 164 of the distal tip portion 130 extends coaxial with the central axis 162 of the main catheter body. Accordingly, such embodiments of the present disclosure also improve the rapid-exchange functionality of the catheter 102 by reducing guidewire binding and catheter prolapse while simultaneously improving patient safety.

However, even in the embodiment of FIG. 7, there remains a reduced bending moment in one axis at the location of the rapid-exchange entry port 132. In that regard, the tubular structure of the distal tip provides a gradually diminishing stiffness as it tapers toward the distal tip, while the proximal shaft maintains a consistent bending stiffness along its length, particularly when the flexible driveshaft is in a distal location to prevent the shaft from collapsing and kinking. However, at the location of the rapid-exchange port 132, the cylindrical or tubular cross-section of the proximal shaft transitions to a u-shape where the notch or opening is formed in the side of the catheter, and then it transitions back to a tubular cross-section along the length of the tip. As a result, some embodiments of the present disclosure combine the offset rapid-exchange arrangement with the reinforcing elements described above to provide a further improved rapid-exchange structure. FIG. 8 illustrates such an embodiment. As shown in FIG. 8, an OCT imaging catheter is provided that includes the distal portion 130 offset relative to the main catheter body such that the lumen 136 of the distal portion 130 is offset relative to the drive shaft 110 and/or central axis 162 of the proximal portion of the catheter 170 and at least one reinforcing element 172 extends within the catheter body adjacent to the rapid-exchange port 132. In particular, in some instances the reinforcing element(s) 172 extend from proximal of the rapid-exchange port 132 to distal of the rapid-exchange port 132 to provide a generally constant bending stiffness or a generally constant change in bending stiffness along the length of the catheter 170.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intravascular imaging device, including:
   a main catheter body comprising a lumen;
   a rotatable driveshaft positioned within the lumen of the main catheter body;
   an imaging element coupled to a distal end of the rotatable driveshaft;
   a distal portion extending from the main catheter body, wherein the distal portion comprises a guidewire lumen and a rapid-exchange port in communication with the guidewire lumen, wherein the guidewire lumen and the rapid-exchange port are sized and shaped to receive a guidewire; and
   at least one reinforcement positioned at the distal portion, wherein the at least one reinforcement is spaced from the rapid-exchange port, the guidewire lumen, and an outer surface of the distal portion such that the at least one reinforcement is embedded within the distal portion, wherein a proximal end of the at least one reinforcement is spaced distally from a distal end of the lumen of the main catheter body by material forming the distal portion and proximally from a proximal end of the rapid-exchange port, and
   wherein a distal end of the at least one reinforcement is spaced distally from a distal end of the rapid-exchange port.

2. The intravascular imaging device of claim 1, wherein the imaging element is an ultrasound transducer.

3. The intravascular imaging device of claim 1, wherein the imaging element is an optical coherence tomography (OCT) element.

4. The intravascular imaging device of claim 1, wherein the guidewire lumen extends coaxial with a central axis of the main catheter body.

5. The intravascular imaging device of claim 1, wherein the guidewire lumen extends offset from and parallel to a central axis of the main catheter body.

6. The intravascular imaging device of claim 1, wherein the at least one reinforcement includes at least one of a wire, a rod, a tapered rod, a tube, a u-shaped trough, or a spring coil.

7. The intravascular imaging device of claim 1, wherein the at least one reinforcement is formed of at least one of a metal, a metal alloy, or a plastic.

8. The intravascular imaging device of claim 1, wherein the at least one reinforcement consists of a single reinforcement.

9. The intravascular imaging device of claim 8, wherein the single reinforcement is centered between a first side and an opposite, second side of the distal portion.

10. The intravascular imaging device of claim 1, wherein the at least one reinforcement comprises two reinforcements.

11. The intravascular imaging device of claim 10, wherein a first of the two reinforcements is positioned proximate to a first side of the distal portion and a second of the two reinforcements is positioned proximate to an opposite, second side of the distal portion.

12. The intravascular imaging device of claim 1, wherein the at least one reinforcement is sized and shaped to provide a constant bending stiffness from a position proximal of the rapid-exchange port to a position distal of the rapid-exchange port.

\* \* \* \* \*